United States Patent [19]

Cluzan et al.

[11] 4,009,174

[45] Feb. 22, 1977

[54] ESTERS OF SUBSTITUTED NICOTINIC ACIDS

[75] Inventors: Robert Cluzan; Lazare Katz, both of Paris, France

[73] Assignee: The Boots Company Limited, Nottingham, England

[22] Filed: Apr. 29, 1974

[21] Appl. No.: 465,219

Related U.S. Application Data

[63] Continuation-in-part of Ser. No. 313,319, Dec. 8, 1972, abandoned, which is a continuation-in-part of Ser. No. 139,963, May 3, 1971, abandoned.

[52] U.S. Cl. .................. 260/293.69; 260/247.2 B; 260/239 BF; 260/268 H; 260/291; 260/295 R; 424/266

[51] Int. Cl.² ..................................... C07D 405/12
[58] Field of Search ..... 260/247.2, 293.69, 295.5 R

[56] References Cited

UNITED STATES PATENTS 2,739,152    3/1956    Krimmel .................... 260/293.69

Primary Examiner—Paul J. Killos
Attorney, Agent, or Firm—Lawrence Rosen; E. Janet Berry

[57] ABSTRACT

Novel derivatives of nicotinic acid possessing vasomotor properties.

3 Claims, No Drawings

ESTERS OF SUBSTITUTED NICOTINIC ACIDS

This application is a continuation-in-part of our application Ser. No. 313,319 filed Dec. 8, 1972, now abandoned; which in turn is a continuation-in-part of our application Ser. No. 139,963 filed May 3, 1971, now abandoned.

This invention relates to novel derivatives of nicotinic acid which have been found to possess biological activity.

According to one aspect of the invention there are provided compounds of general formulae I – V

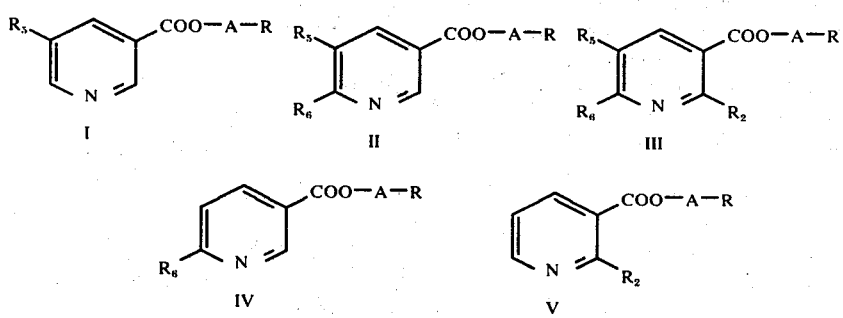

in which
- $R_5$ is an optionally substituted aryl group or a heterocyclic group;
- $R_2$ and $R_6$ are optionally substituted aliphatic radicals containing 1-20 carbon atoms in the aliphatic moiety;
- R is selected from di(lower alkyl)amino, pyrrolidino piperidino, hexamethyleneimino, morpholino, piperazino and 4'-(lower alkyl)piperazino;
and A is an alkylene group containing 2-20 carbon atoms; together with pharmaceutically acceptable acid addition salts thereof.

Examples of $R_5$ are phenyl, methoxyphenyl, dimethoxyphenyl, trimethoxyphenyl and pyridyl.

Examples of $R_2$ and $R_6$ are alkyl, optionally substituted arylalkyl and optionally substituted arylalkenyl. More specifically, examples include lower alkyl (especially methyl), styryl, styryl containing 1-3 methoxy substituents in the phenyl ring, phenethyl and phenethyl containing 1-3 methoxy substituents in the phenyl ring.

Examples of A are ethylene and propylene, preferred groups.

Examples of R include dimethylamino and diethylamino. Typical combinations of R and A include 2-(N,N-dimethylamino)-ethyl and -propyl-, 3-(N,N-dimethylamino)propyl-, and the corresponding diethyl analogues; 2-(pyrrolidino)ethyl- and -propyl-, 2-(pyrrolidino)propyl and similar combinations wherein pyrrolidino is replaced by piperidino, hexamethyleneimino, morpholino, piperazino and 4'-lower alkylpiperazino.

The invention includes pharmaceutically acceptable acid addition salts of the compounds of general formulae I-V. It is not possible to be too specific about these salts because, for example, the hydrochloride of one of the compounds may be perfectly stable and pharmaceutically acceptable whereas the hydrochloride of another of the compounds may be extremely hygroscopic and therefore unlikely to be pharmaceutically acceptable. With this in mind, some typical salts falling within the invention include hydrochlorides, maleates, succinates, citrates and camphosulphonates. Ease of crystallizability is another factor which must be considered. Details of many specific salts will be found in the examples at the end of this specification, but the acids used therein and which are listed above are only typical acids and are not intended to imply that the invention is limited to salts with these particular acids.

Typical methods for the preparation of the compounds of the invention are as follows: [For the sake of brevity, the substituted pyridine nuclei of general formulae I—V (less the —COO-A-R moiety) will be designated "B" from now on where convenient.]

1. Trans-esterification of a compound of general formula VI

$$B - COOR_7 \qquad \text{VI}$$

in which $R_7$ is lower alkyl, preferably methyl or ethyl, with the required amino-alcohol of general formula VII

$$R - A - OH \qquad \text{VII}$$

in which R and A are as hereinbefore defined. This is carried out by heating such that the alcohol $R_7OH$ which forms is readily eliminated by distillation as it is evolved during the reaction;

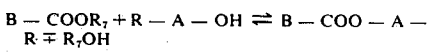
$$B - COOR_7 + R - A - OH \rightleftarrows B - COO - A - R \mp R_7OH$$

In this way, and additionally by using an excess of the amino-alcohol as reaction medium, the equilibrium can be displaced towards the required product. Preferably a catalytic amount of sodium or the like should be present.

The temperature required to achieve the desired result and the length of time of heating will naturally vary to some extent with the different values of B — $COOR_7$ and R — A — OH, but, in general, a temperature of at least 70° C. for at least 2 hours is advisable. For preference, to speed up the reaction and to ensure maximum yields, temperatures of the order of 120°-180° C. are used for periods of 5-9 hours. However, we do not intend to be limitative by these statements; optimum conditions for each compound are readily found by experimentation.

2. Reaction of an acid chloride of general formula VIII

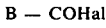
$$B - COHal \qquad \text{VIII}$$

in which Hal is a halogen atom, preferably chlorine, with the required amino-alcohol of general formula VII hereinbefore described, optionally in an inert organic solvent such as benzene. Exact reaction conditions will be readily apparent to or readily ascertainable by a person skilled in the art.

3. Continuous azeotropic distillation with a neutral solvent boiling above 130° C. (preferably 130°–160° C.) of a mixture of an acid of general formula IX

B — COOH     IX and an amino-alcohol of general formula VII hereinbefore described. Examples of suitable solvents are xylene, chlorobenzene, ethylbenzene and cumene.

4. Pharmaceutically acceptable salts of the bases prepared as described in (1) – (3) above are prepared by conventional methods. Thus, for example, a base may be dissolved in a suitable inert solvent such as a lower alkanol (e.g. isopropanol) or tetrahydrofuran and the required acid added. Frequently the desired salt precipitates immediately or upon evaporation of some of the solvent; in other cases the addition of ether is necessary to cause precipitation of the salt.

It will be appreciated that the preferred method from the above methods (1) – (3) for any particular compound of general formulae I–V will depend upon the type of compound required. The choice and exact reaction conditions will be readily apparent to those skilled in the art from inherent knowledge, the prior art literature, the brief descriptions given above and the examples at the end of this specification.

The starting materials of the aforementioned general formulae VI, VIII and IX are prepared by methods known in the art of pyridine chemistry. Many such materials have already been described in the literature. Some typical methods are the following:

a. A lower alkyl, preferably methyl or ethyl, ester of an acetic acid containing in the 2-position an $R_5$ group and the aldehyde group is condensed with cyanoacetamide to yield a 2,6-dihydroxynicotinonitrile with $R_5$ in position 5. After alcoholysis to produce the corresponding lower alkyl, preferably methyl or ethyl, ester of 2,6-dihydroxy-5-$R_5$-nicotinic acid, chlorination e.g. with phosphorus oxychloride gives the corresponding 2,6-dichloro-compound, which is finally hydrogenolysed to give a lower alkyl ester of 5-$R_5$-nicotinic acid.

b. A 3-(N,N-dimethylamino)-2-$R_5$-acrolein is condensed with cyanoacetamide to give a 2-hydroxynicotinonitrile with $R_5$ in position 5. Alcoholysis, chlorination and hydrogenolysis as in (a) finally yields a lower alkyl ester of 5-$R_5$-nicotinic acid.

c. A methyl $R_6$ ketone with an $R_5$ group and the aldehyde group on the methyl group is condensed with cyanoacetamide to give 2-hydroxy-5-$R_5$-6-$R_6$-nicotinonitrile. Alcoholysis, chlorination and hydrogenolysis as in (a) finally yields a lower alkyl ester of 5-$R_5$-6-$R_6$-nicotinic acid.

d. A methyl $R_6$ ketone with an $R_5$ group and the aldehyde group on the methyl group is condensed with an enamine of general formula X

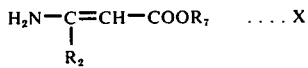

to give a lower alkyl ester of 2-$R_2$-5-$R_5$-6-$R_6$-nicotinic acid.

e. 6-$R_6$-3-ethylpyridine is oxidised e.g. with potassium permanganate to give 6-$R_6$-nicotinic acid, which may then be esterified if desired.

f. The reactions schematically represented below:

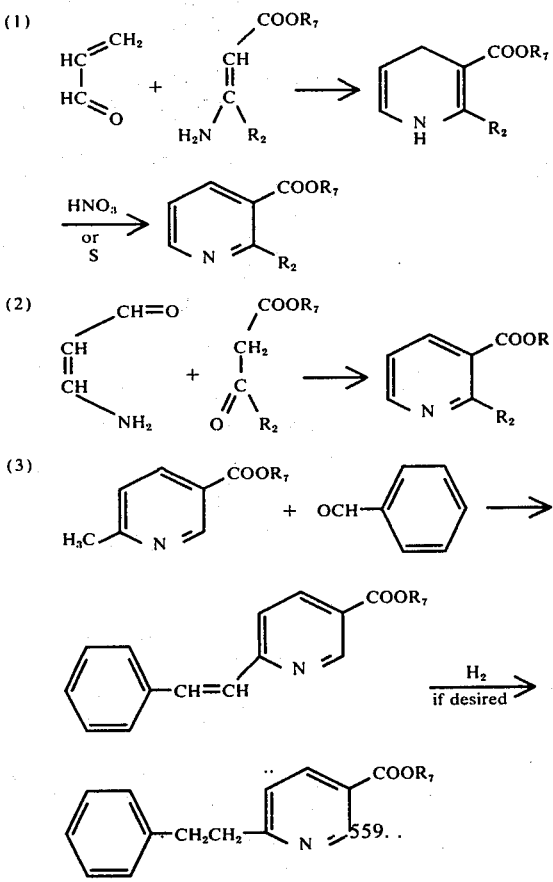

4. As (3) but with the —$CH_3$ group in the 2-position in place of the 6-position.

It will be appreciated that all the methods (a)–(f) outlined above are not applicable to all the starting materials of general formulae VI, VIII and IX. The preferred method for any particular compound will depend upon the type of starting material required; the choice and reaction conditions will be readily apparent to those skilled in the art.

It has been found that the compounds of the invention possess vasomotor properties. The compounds are vasodilators, in particular peripheral vasodilators, and may be used in the treatment of disorders of circulatory origin. The vasodilator activity of compounds of the invention in mammals has been demonstrated in experiments involving mice as standard laboratory animals.

According to a further feature of the invention there are provided therapeutic compositions which comprise a compound of the invention in association with a pharmaceutically acceptable excipient, i.e. a pharmaceutically acceptable carrier. The compositions may be used for oral, rectal or parenteral administration. The compositions preferably contain 0.1–90% by weight of a compound of the invention.

Compositions for oral administration are the known pharmaceutical forms for such administration, such as for example tablets, capsules, syrups, and aqueous and oily suspensions. The excipients used are the excipients known in the pharmacist's art. Thus, for example, tablets comprise a compound of the invention mixed with a conventional diluent such as lactose and a disintegrating agent such as maize starch and a lubricating agent such as magnesium stearate. Such tablets may if desired be provided with enteric coatings by known methods, for example by the use of cellulose acetate phthalate. Similarly capsules, for example hard or soft gelatin capsules, containing a compound of the invention, with or without other excipients, may be prepared by conventional means and, if desired provided with enteric coatings. The tablets and capsules may conveniently contain 10–500 mg. of a compound of the invention.

Composition for rectal administration are the known pharmaceutical forms for such administration, such as for example suppositories with cocoa butter or polyethylene glycol bases.

Compositions for parenteral administration, e.g. intravenous injection, are the known pharmaceutical forms for such administration, for example sterile solutions in normal saline for injection or sterile solutions in propylene glycol.

It will be appreciated that because of their physical characteristics (crystalline powders), the pharmaceutically acceptable acid addition salts hereinbefore described are to be preferred in most cases to the bases themselves (high boiling liquids). The pharmacological activity of the pharmaceutically acceptable acid addition salts of the invention is due to the base component of the salts.

The compositions hereinbefore described may be provided in dosage unit forms containing 70 mg. – 14 g., more usually 140 mg. – 1.4 g., optionally in divided dosage unit form.

According to another feature of the invention there is provided a method of treating disorders of circulatory origin which comprises administering to a subject suffering from such disorders a peripheral vasodilating amount of a compound of the invention. Doses vary according to the activity of the particular compound, but in general fall within broad range of 1–200 mg./kg., more usually within the range 2–20 mg./kg.

The following non-limitative examples illustrate the invention.

EXAMPLE 1

3-N,N-Dimethylaminopropan-1-ol (13.4 g.) and sodium (0.07 g.) were added to a 100 ml. flask fitted with an inlet for dry nitrogen and provided with distillation means. After heating at about 50° C. until the sodium had dissolved, methyl 5-phenyl-6-methylnicotinate (10 g.) was added and heating continued for 9 hours at about 180° C.; methanol distilled off. After cooling, excess of the sodium aminoalcoholate was precipitated by the addition of dry ether (200 ml.) and filtered off. Evaporation of the ether and distillation of the residue in vacuo gave 3-N,N-dimethylaminopropyl 5-phenyl-6-methylnicotinate, b.p. 145°–150° C./ 0.01 mm.

The dihydrochloride was made by conventional means, m.p. 148° C. (isopropanol/ether).

By a similar technique, the compounds listed below were prepared.

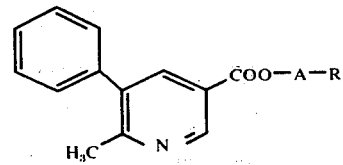

| R | A | b.p. ester (° C./mm.) | Salt | m.p. Salt (° C) |
|---|---|---|---|---|
| Me₂N— | —(CH₂)₂— | 150–155/0.01 | dihydrochloride | 186 |
| Me₂N— | " | 165–170/0.01 | " | 146 |
| pyrrolidinyl-N— | " | 190–195/0.02 | " | 180 |
| piperidinyl-N— | " | 190–192/0.01 | " | 168 |
| morpholinyl-N— | " | 200/0.1 | " | 178 |
| Me-N-piperazinyl-N— | " | 210–215/0.1 | trihydrochloride | 165 |
| Et₂N— | —(CH₂)₃— | 165–170/0.02 | dihydrochloride | 156 |
| pyrrolidinyl-N— | " | 185–190/0.1 | " | 165 |
| piperidinyl-N— | " | 195–200/0.01 | " | 162 |

-continued

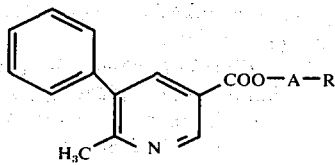

| R | A | b.p. ester (° C./mm.) | Salt | m.p. Salt (° C) |
|---|---|---|---|---|
| morpholino- | " | 195/0.02 | " | 160 |
| Me—N(piperazine)N— | " | 210–215/0.1 | trihydrochloride | 204 |
| Et₂N— | —CH(CH₃)CH₂— | 140–150/0.01 | dihydrochloride | 174 |

EXAMPLE 2

The apparatus and procedure of Example 1 were used, employing 3-N,N-dimethylaminopropan-1-ol (15.5 g.) sodium (0.07 g.), ethyl 2,6-dimethyl-5-phenylnicotinate (12.75 g.), and a temperature of 170°–180° C. for about 8 hours. There was thus obtained 3-N,N-dimethylaminopropyl 2,6-dimethyl-5-phenylnicotinate, b.p. 160°–170° C./0.15 mm.; citrate, m.p. 70° C. (isopropanol/ether).

The compounds listed below were similarly prepared.

| R | A | b.p. ester (° C./mm.) | Salt | m.p. salt (° C.) |
|---|---|---|---|---|
| Me₂N— | —(CH₂)— | 160–170/0.1 | disuccinate | 120 |
| Et₂N— | " | 190/0.2 | dihydrochloride | 154 |
| pyrrolidino- | " | 170–172/0.1 | " | 158 |
| piperidino- | " | 150–160/0.05 | disuccinate | 136 |
| morpholino- | " | 190–195/0.15 | dihydrochloride | 145 |
| Me—N(piperazine)N— | " | 195–198/0.1 | trihydrochloride | 180 |
| Et₂N— | —(CH₂)₃— | 147–150/0.01 | dihydrochloride | 146 |
| pyrrolidino- | —(CH₂)₃— | 195/0.05 | disuccinate | 118 |
| piperidino- | " | 190–195/0.05 | " | 104 |
| morpholino- | " | 198–200/0.1 | dihydrochloride | 174 |
| Me—N(piperazine)N— | " | 210–215/0.1 | trisuccinate | 110 |

EXAMPLE 3

The apparatus and procedure of Example 1 were used, employing 2-N,N-dimethylaminoethan-1-ol (9 ml.), sodium (0.07 g.), methyl 5-phenylnicotinate (4.1 g.), and a temperature of 120°–125° C. for 7.5 hours. The crude 2-N,N-dimethylaminoethyl 5-phenylnicotinate obtained as an oil was not distilled, but was used directly for the preparation of the maleate, m.p. 126° C. (tetrahydrofuran/ether).

The compounds listed below were similarly prepared.

EXAMPLE 4

The apparatus and procedure of Example 1 were used, employing 3-N,N-dimethylaminopropan-1-ol (15.45 g.), sodium (0.07 g.), methyl 6-methylnicotinate (7.56 g.), and a temperature of 140° C. for 5-6 hours. There was thus obtained 3-N,N-dimethylaminopropyl 6-methylnicotinate, b.p. 125° C./0.1 mm.; maleate, m.p. 114° C.

The compounds listed below were similarly prepared.

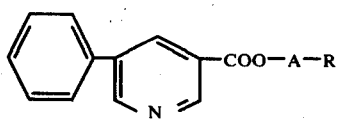

| R | A | Salt | m.p. salt (° C) |
|---|---|---|---|
| Et$_2$N— | —(CH$_2$)$_2$— | maleate | 53 |
| pyrrolidino-N— | " | " | 115 |
| piperidino-N— | " | " | 120 |
| morpholino-N— | " | dihydrochloride | 180 |
| Me—N(piperazino)N— | " | trihydrochloride | 200 |
| Me$_2$N— | —(CH$_2$)$_3$— | maleate | 99 |
| Et$_2$N— | " | " | 144 |
| pyrrolidino-N— | " | " | 104 |
| piperidino-N— | " | " | 91 |
| morpholino-N— | " | " | 69 |
| Me—N(piperazino)N— | " | trihydrochloride | 200–210 |
| Et$_2$N— | —CH(CH$_3$)CH$_2$— | dihydrochloride | 170 |

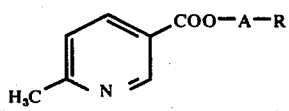

| R | A | b.p. ester (° C/mm.) | Salt | m.p. salt (° C.) |
|---|---|---|---|---|
| Me$_2$N— | —(CH$_2$)$_2$— | 116/0.1 | maleate | 126 |
| Et$_2$N— | " | 96–97/0.04 | " | 88 |
| pyrrolidino-N— | " | 149–152/3.0 | dihydrochloride | 140–144 |

-continued

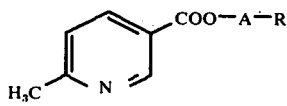

| R | A | b.p. ester (° C/mm.) | Salt | m.p. salt (° C.) |
|---|---|---|---|---|
| piperidinyl | " | 152/1.5 | " | 169–172 |
| morpholinyl | " | 173/3.0 | " | 196–198 |
| Me-N-piperazinyl | " | 150/0.3 | dimaleate | 201–202 |
| Et₂N— | —(CH₂)₃— | 110/0.4 | — | — |
| pyrrolidinyl | —(CH₂)₃— | 134/0.15 | maleate | 110 |
| piperidinyl | " | 168/0.3 | dihydrochloride | 180 |
| morpholinyl | " | 148/0.15 | maleate | 141 |
| Me-N-piperazinyl | " | 135/0.05 | trisuccinate | 132 |
| Et₂N— | —CH(CH₃)CH₂— | 106/0.02 | maleate | 120 |

EXAMPLE 5

The apparatus and procedures of Example 3 were used, employing 2-(N-methyl-N'-piperazinyl)ethan-1-ol (42.7 g.), sodium (0.2 g.), methyl 6-p-methoxystyrylnicotinate (13.46 g.), and a temperature of 70° C. for 8 hours. The crude ester was treated to give the dimaleate of N-methyl-N'-ethylpiperazine 6-p-methoxystyrylnicotinate, m.p. 214°–215° C.

The starting material was prepared by refluxing for 72 hours a mixture of methyl 6-methylnicotinate (60.4 g.), anisaldehyde (163.3 g.), acetic anhydride (120 ml.) and xylene (320 ml.). Steam distillation was used to remove the excess anisaldehyde, the acetic acid formed during the reaction and xylene. The residue was dried in the cold, washed with ether, and dried at 60° C. for 12 hours to give methyl 6-p-methoxystyrylnicotinate, m.p. 170° C.

The compounds listed below were similarly prepared.

| R | A | Salt | m.p. salt (° C.) |
|---|---|---|---|
| Me₂N— | —(CH₂)₂— | maleate | 168 |
| Et₂N— | " | " | 119 |
| pyrrolidinyl | " | " | 149 |
| piperidinyl | " | dihydrochloride | 177–180 |
| morpholinyl | " | maleate | 164 |
| Me₂N— | —(CH₂)₃— | " | 162 |
| Et₂N— | " | " | 105 |

-continued

| | CH₃O–⟨phenyl⟩–CH=CH–⟨pyridine-N⟩–COO–A–R | | |
|---|---|---|---|
| R | A | Salt | m.p. salt (° C.) |
| pyrrolidin-1-yl | '' | '' | 137 |
| piperidin-1-yl | '' | '' | 146 |
| morpholin-4-yl | '' | '' | 151 |
| 4-methylpiperazin-1-yl | '' | dimaleate | 212–214 |
| Et₂N— | —CH(CH₃)CH₂— | maleate | 84 |

EXAMPLE 6

The apparatus and procedures of Example 3 were used, employing 2-(N-methyl-N'-piperazinyl)ethan-1-ol (21.35 g.), sodium (0.1 g.), methyl 6-p-methoxyphenethylnicotinate (13.56 g.), and a temperature of 170° C. for 6 hours. The crude ester was treated to give the dimaleate of N-methyl-N'-ethylpiperazine 6-p-methoxyphenethylnicotinate, m.p. 200° C.

The starting material was prepared by hydrogenating for 4 hours at ordinary pressure and room temperature methyl 6-p-methoxystyrylnicotinate (25 g.) in tetrahydrofuran (300 ml.) in the presence of Raney nickel (10 g.). After filtration and removal of the solvent in vacuo, the residue was crystallised from hexane (500 ml., with active carbon) to give methyl 6-p-methoxyphenethylnicotinate, m.p. 82° C.

The compounds listed below were similarly prepared.

| | CH₃O–⟨phenyl⟩–CH₂–CH₂–⟨pyridine-N⟩–COO–A–R | | |
|---|---|---|---|
| R | A | Salt | m.p. salt (° C.) |
| Me₂N— | —(CH₂)₂— | maleate | 118 |
| Et₂N— | '' | '' | 62–63 |
| pyrrolidin-1-yl | '' | '' | 125 |
| piperidin-1-yl | '' | '' | 136 |
| morpholin-4-yl | '' | '' | 134 |
| Me₂N— | —(CH₂)₃— | maleate | 96–97 |
| Et₂N— | '' | '' | 65 |
| '' | '' | '' | 82 |
| pyrrolidin-1-yl | '' | '' | 104 |
| piperidin-1-yl | '' | '' | 109 |
| morpholin-4-yl | '' | '' | — |
| 4-methylpiperazin-1-yl | '' | dimaleate | 206 |

EXAMPLE 7

The apparatus and procedure of Example 1 were used, employing 2-morpholinoethan-1-ol (20.7 g.), sodium (0.07 g.), ethyl 2-methylnicotinate (27.18 g.), and a temperature of 160°–170° C. for 6 hours. There was thus obtained 2-morpholinoethyl 2-methylnicotinate, b.p. 130° C./0.08 mm.; maleate, m.p. 150° C.

The compounds listed below were similarly prepared.

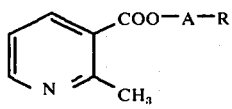

| R | A | b.p. ester (° C./mm.) | Salt | m.p. salt (° C.) |
|---|---|---|---|---|
| Me₂N— | —(CH₂)₂— | 65/0.09 | maleate | 91 |
| Et₂N— | " | 108/0.08 | " | 84 |
| pyrrolidino | " | 120/0.04 | " | 111 |
| piperidino | " | 120/0.05 | dimaleate | 128 |
| Me—N(piperazino)— | " | 125/0.02 | " | 157 |
| Me₂N— | —(CH₂)₃— | 100/0.09 | maleate | 129 |
| Et₂N— | " | 116–120/0.8 | " | 99 |
| pyrrolidino | " | 140–142/0.2 | " | 96 |
| piperidino | " | 128/0.05 | " | 118 |
| morpholino | " | 130/0.05 | " | 120 |
| Me—N(piperazino)— | " | 158–160/0.05 | dimaleate | 189 |
| Et₂N— | —CH(CH₃)CH₂— | 100/0.07 | maleate | 86 |

EXAMPLE 8

The compounds listed below were prepared by the following general method. The amino-alcohol (0.08 mol.) in dry benzene (100 ml.) was cooled to 5°–10° C., and the appropriate substituted nicotinoyl chloride (0.02 mol.) was added portion-wise with stirring. The reaction mixture was then stirred at 5°–10° C. for 1 hour and then at room temperature for 12 hours, washed with 10% aqueous sodium carbonate (3 × 100 ml.) and dried over anhydrous sodium sulphate. Evaporation of the solvent and removal of the excess of amino-alcohol by distillation at 150°–160° C. in vacuo gave the desired ester as a non-distillable oil.

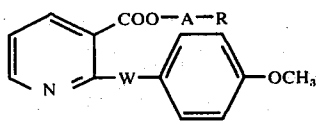

| R | A | W | Salt | m.p. salt (° C.) |
|---|---|---|---|---|
| Me₂N— | —(CH₂)₂— | —CH=CH— | maleate | 150 |
| Et₂N— | " | " | dihydrochloride | 188 |
| pyrrolidino | " | " | maleate | 90 |
| piperidino | " | " | " | 88–90 |
| morpholino | " | " | " | 137 |
| Me—N(piperazino)— | " | " | dimaleate | 186 |

-continued structure:

| R | A | W | Salt | m.p. salt (° C.) |
|---|---|---|---|---|
| Me₂N— | —(CH₂)₃— | —CH=CH— | maleate | 92 |
| Et₂N— | " | " | " | 62 |
| pyrrolidino | " | " | " | 72 |
| piperidino | " | " | " | 100 |
| morpholino | " | " | " | 136 |
| Me—N-piperazino | " | " | dimaleate | 187 |
| Me₂N— | —(CH₂)₂— | —CH₂CH₂— | maleate | 107 |
| Et₂N— | " | " | " | 108 |
| pyrrolidino | " | " | " | 128 |
| piperidino | " | " | " | 126 |
| morpholino | " | " | " | 112 |
| Me—N-piperazino | " | " | dimaleate | 172 |
| Me₂N— | —(CH₂)₃— | " | maleate | 72 |
| Et₂N— | " | " | " | 50–54 |
| pyrrolidino | —(CH₂)₃— | —CH₂CH₂— | dihydrochloride | 131 |
| piperidino | " | " | maleate | 66 |
| morpholino | " | " | " | 112 |
| Me—N-piperazino | " | " | dimaleate | 184 |

[All the compounds of the invention described in Examples 1–8 gave satisfactory elemental analyses and their structures have been verified by infra-red spectroscopy.]

EXAMPLE 9

In the preparation of tablets, mixtures of the following type may be tableted in conventional manner:

| | |
|---|---|
| Pharmaceutically acceptable salt of the invention | 10–90% |
| Lactose | 0–80% |
| Maize starch | 5–10% |
| Magnesium stearate | ca. 1% |
| Microcrystalline cellulose | 0–90% (by weight) |

EXAMPLE 10

In the preparation of capsules, a salt of the invention may be mixed with an equal weight of lactose and the mixture encapsulated in hard gelatin capsules.

EXAMPLE 11

In the preparation of 1 g. suppositories, bases of the following type may be used, each suppository containing for example 200 mg. of a salt of the invention:

| | |
|---|---|
| Polyethylene glycol 4000 | 33% |
| Polyethylene glycol 6000 | 47% |
| Water | 20% |

EXAMPLE 12

Solutions for parenteral injection may be prepared comprising 4 mg. of a salt of the invention per ml. of normal saline for injection B.P.

EXAMPLE 13

A solution for parenteral injection is prepared by dissolving 3-morpholinopropyl 6-methylnicotinate monomaleate in water for injection B.P. to a concentration of 5 mg. per ml. and then sterilizing the solution by filtration.

EXAMPLE 14

A solution for parenteral injection is prepared by dissolving 3-piperidinopropyl 2-methylnicotinate monomaleate in water for injection B.P. to a concentration of 5 mg. per ml. and then sterilizing the solution by filtration.

We claim:
1. A compound of the formula

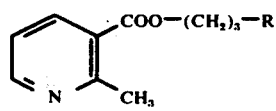

and pharmaceutically acceptable acid addition salts thereof, in which R is piperidino or pyrrolidino.
2. A compound according to claim 1 in which R is piperidino.
3. 3-Piperidinopropyl 2-methylnicotinate.

* * * * *